United States Patent [19]

Hakky

[11] Patent Number: 4,602,621
[45] Date of Patent: Jul. 29, 1986

[54] MANUALLY ACTUATED, SELF CONTAINED PENILE IMPLANT

[76] Inventor: Said I. Hakky, 185 Dagenham Rd., Rush Green, Romford, Essex RM7 0TL, England

[21] Appl. No.: 683,286

[22] Filed: Dec. 18, 1984

[51] Int. Cl.⁴ .............................................. A61F 5/00
[52] U.S. Cl. ................................................. 128/79
[58] Field of Search ................................... 128/79; 3/1

[56] References Cited

U.S. PATENT DOCUMENTS

| | | | |
|---|---|---|---|
| 3,954,102 | 5/1976 | Buuck | 128/79 |
| 4,009,711 | 3/1977 | Uson | 128/79 |
| 4,267,829 | 5/1981 | Burton et al. | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,369,771 | 1/1983 | Trick | 128/79 |
| 4,378,792 | 4/1983 | Finney | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |

Primary Examiner—Robert Peshock
Assistant Examiner—Cary E. Stone
Attorney, Agent, or Firm—Caesar, Rivise, Bernstein & Cohen

[57] ABSTRACT

A self-contained penile prosthesis comprising at least one cylinder for implantation in the penis and including a front tip section, an intermediate section, and a rear tail section. The intermediate section includes a tubular chamber which is inflatable, and arranged to assume an elongated rigid and hard state from a flexible, flaccid state upon the application of an operating liquid under pressure thereto. The tip section includes a portion which is arranged to be manually twisted through an acute angle to cause a substantial volume of operating liquid to be transferred by piston means from a reservoir into the inflatable chamber.

21 Claims, 6 Drawing Figures

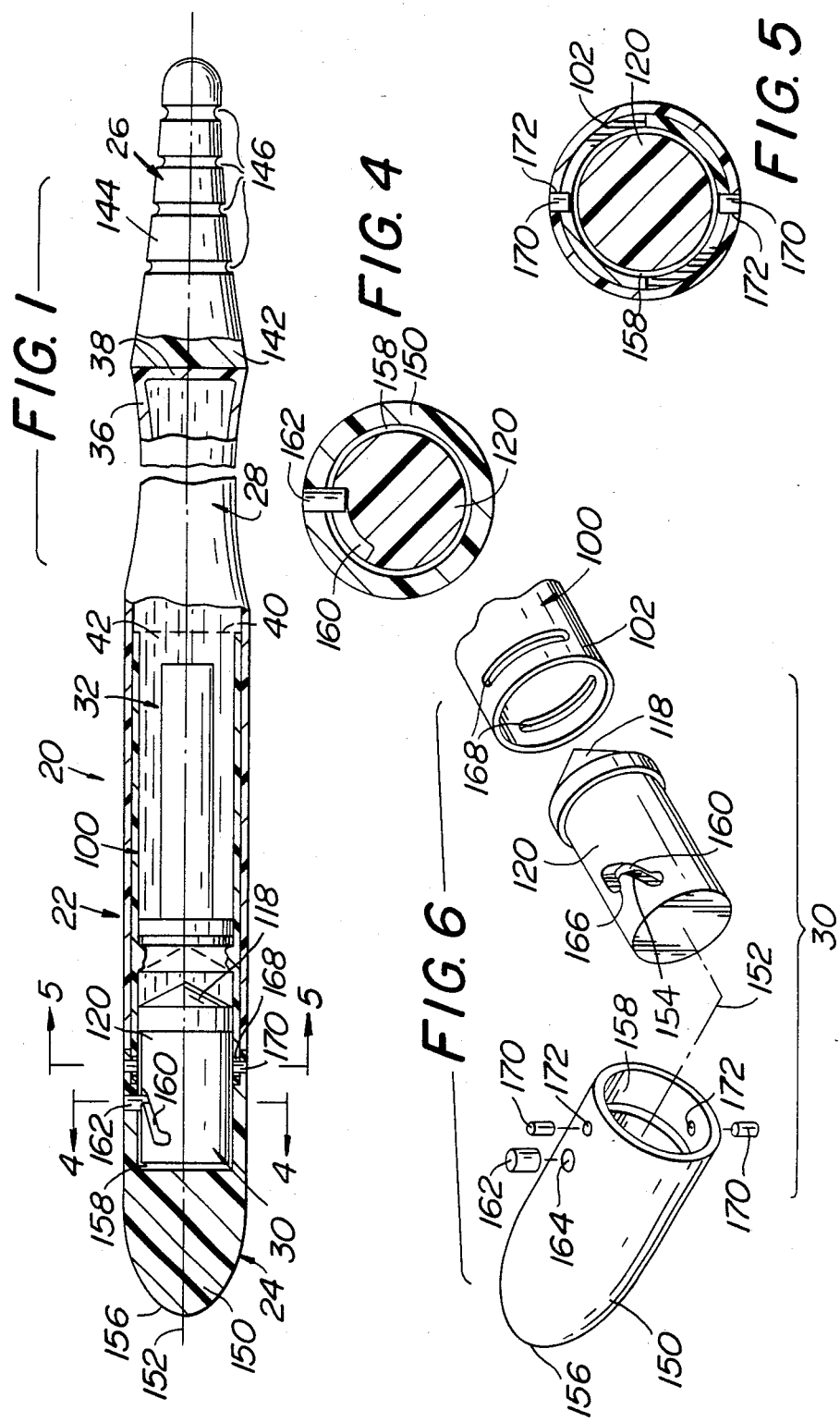

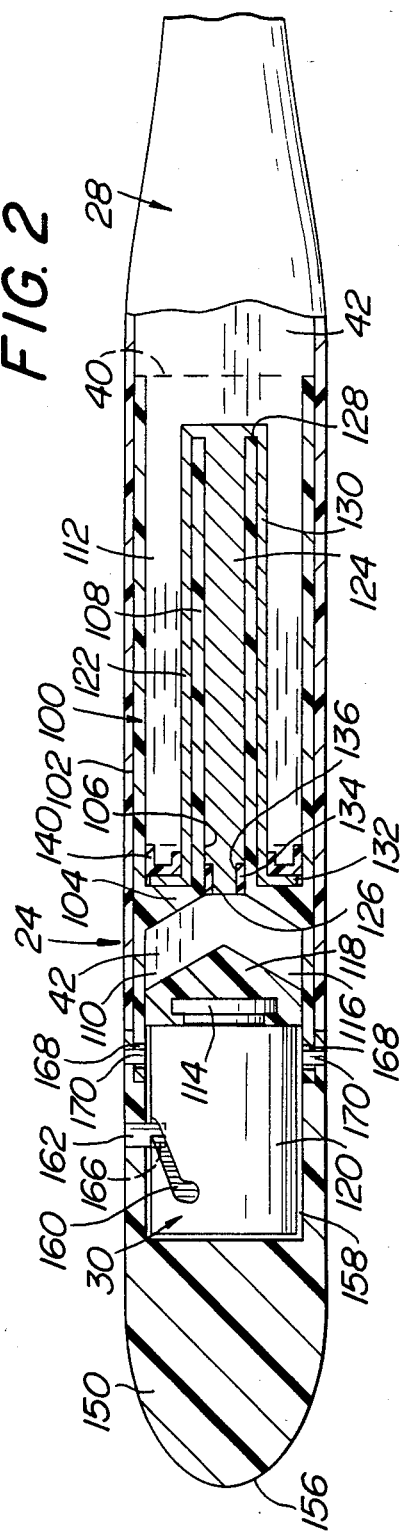
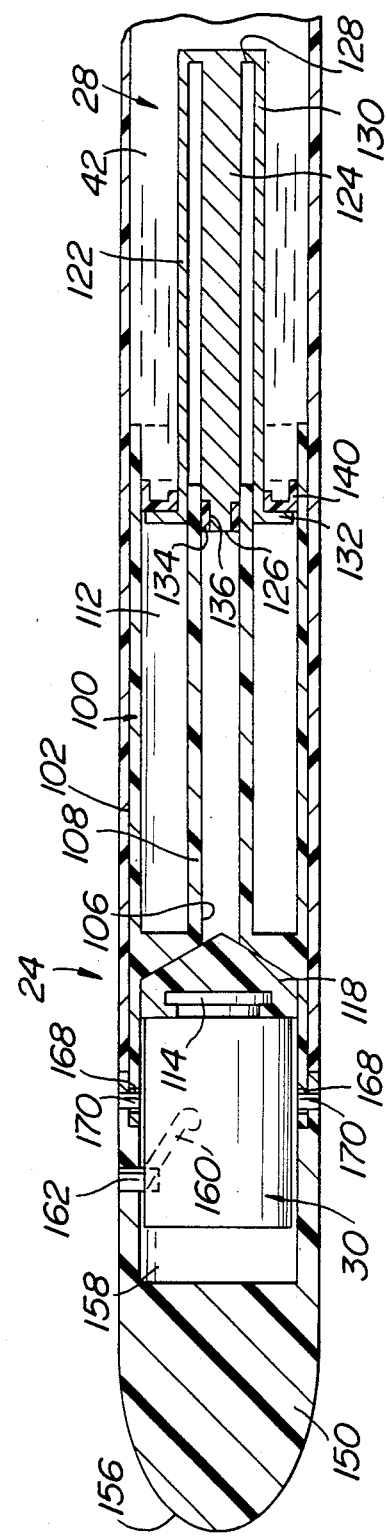

MANUALLY ACTUATED, SELF CONTAINED PENILE IMPLANT

BACKGROUND OF THE INVENTION

This invention relates generally to implantable penile prostheses and more particularly to implantable, self-contained penile prostheses.

Various penile implants have been disclosed in the patent literature and are commercially available for curing erectile impotence. Such devices basically comprise a pair of cylinders each of which adapted to be implanted in a respective corpus cavernosum of the penis. Each cylinder includes a hollow portion arranged to be pressurized by the pumping of a liquid therein. When the cylinder portions are pressurized the penis assumes an erect, rigid state. The liquid used to inflate the cylinders is provided via respective tubes from a liquid supply reservoir. A pump and a reversible, one-way valve, are also included in the prosthesis and are typically arranged to be implanted in the scrotum and/or the abdomen. The pump and valve enable the liquid to be carried from the reservoir into the cylinder to cause the erection when the valve is in a first setting. In order to render the penis flaccid the valve is arranged to be actuated to enable the liquid to pass through it in the opposite direction so that operation of the pump carries the liquid back into the reservoir.

Examples of penile implants utilizing the foregoing technology are shown in U.S. Pat. Nos. 3,954,102 (Buuck), 4,009,711 (Uson), 4,267,829 (Burton et al.), and 4,342,308 (Trick). While the foregoing pump-type inflatable penile implants all operate on the same basic principle each of those devices include some different structural features, e.g., reinforcing or constraining materials surrounding the inflatable chamber, cylinders including rigid (solid) tip and tail portions, special actuating valves, etc., all in the interest of providing a device which will closely simulate a natural erection, is easy to operate, and which exhibits a long service life.

While the penile implants such as described above have proven suitable for their intended purposes, they nevertheless leave something to be desired from the standpoint of simplicity of construction and ease of operation. In this regard all of the above identified prior art implants require the use of not only the inflatable cylinders which are to be located within the penis, but also a control valve, pump and reservoir, all of which are implanted within the body remote from the penis. Moreover, operation of such remotely located pump-type penile implants requires the user to first manually operate the valve to its appropriate setting to enable flow from the reservoir to the cylinders and then to manually pump the liquid into cylinders to cause the penis to become erect for sexual intercourse. In order to render the penis flaccid the valve has to be manually returned to its initial position to enable the liquid to flow therethrough in the opposite direction so that operation of the pump carries the liquid from the cylinders back into the reservoir.

Another type of penile prosthesis has been disclosed in various patents. That alternative penile prosthesis constitutes a variation of the externally located pump-type device. In this regard the alternative type penile implant utilizes a pump and reservoir which are both located within the cylinder, with the pump in either the tip portion or an intermediate portion and with the reservoir located within the intermediate or rear portion. Thus the entire prosthesis is self-contained within the cylinder and does not require the use of remotely located reservoirs/valves/pumps. Operation of such a selfcontained type of penile prosthesis is effected by squeezing the portion of the cylinder containing the pump to operate it to cause liquid to flow from the reservoir into an inflatable chamber located at an intermediate point in the cylinder to cause the cylinder to become erect. While this type of penile implant offers the advantage of simplicity of construction over remotely located pump-type implants, it still leaves something to be desired from the standpoint of functionality, simplicity of construction, and ease of operation. Examples of the selfcontained penile prosthesis are shown in U.S. Pat. Nos. 4,353,360 (Finney et al), 4,360,010 (Finney), 4,369,771 (Trick), and 4,399,811 (Finney et al).

Other types of prior art penile prostheses are shown in U.S. Pat. Nos. 4,378,792 (Finney) and 4,383,525 (Burton et al.).

OBJECTS OF THE INVENTION

Accordingly, it is the general object of the instant invention to provide a self-contained penile implant which overcomes the disadvantages of the prior art.

It is a further object of the instant invention to provide a self-contained penile implant which is simple in construction.

It is a further object of the instant invention to provide a self-contained penile prosthesis which is readily adapted to assume an erect rigid state with a simple movement of a portion thereof.

It is a further object of the instant invention to provide a self-contained penile prosthesis which includes an inflatable section and means for transferring a substantial volume of an operating fluid to said inflatable section to render it stiff and erect upon the application of limited movement to that means.

SUMMARY OF THE INVENTION

An implantable penile prosthesis comprising an elongated cylinder having a front portion for disposition in the distal portion of the penis, a rear portion for disposition inside the proximal portion of the penis and an inflatable section located therebetween. The inflatable section is a hollow member. The cylinder includes manually operable actuating means comprising displacement means for longitudinal movement a first predetermined distance toward one end of the cylinder and a hydraulic chamber of a first predetermined volume and having a hydraulic fluid therein. A first piston is coupled to the displacement means. The cylinder also includes fluid reservoir means coupled to the inflatable section, with the fluid reservoir means being of a second predetermined volume and having an operating fluid therein. The second volume is substantially greater than the first volume. A second piston is provided coupled to the hydraulic chamber. The first piston moves in response to the movement of the displacement means to cause the hydraulic fluid to be expelled from the hydraulic chamber, whereupon the second piston means moves to cause the operating fluid in the fluid reservoir means to be provided to the inflatable section to pressurize it, whereupon it moves from a non-erect, flaccid state to an erect, rigid state.

DESCRIPTION OF THE DRAWING

Other objects and many of the attendant advantages of the instant invention will be readily appreciated when the same becomes better understood by reference to the following detailed description when considered in connection with the accompanying drawing wherein:

FIG. 1 is a side elevational view, partial broken away, showing one cylinder of a prosthesis constructed in accordance with this invention in its flaccid state;

FIG. 2 is an enlarged side elevational view partially in section of a portion of the device shown in FIG. 1 and in its flaccid state;

FIG. 3 is a view similar to that of FIG. 2 but showing the device in its erect state;

FIG. 4 is an enlarged sectional view taken along line 4—4 of FIG. 1;

FIG. 5 is an enlarged sectional view taken along line 5—5 of FIG. 1; and

FIG. 6 is an exploded perspective view of a portion of the device shown in FIG. 1.

DETAILED DESCRIPTION OF THE PREFERRED EMBODIMENT

Referring now in greater detail to the various figures of the drawing wherein like reference characters refer to like parts, there is shown an implantable penile prosthesis 20 constructed in accordance with the subject invention. The prosthesis 20 basically comprises an elongated cylindrical member 22 having a substantially rigid front or tip section 24, a substantially rigid rear or tail section 26 and an inflatable intermediate section 28. In normal practice two such cylinders 22 are utilized to make up a complete penile prosthesis. In such a case each cylinder is surgically implanted longitudinally in a respective corpus cavernosum (not shown) of the penis, with the tip section 24 located within the distal portion of the penis and with the tail section 26 located within the proximal portion of penis. The tip section 24 is formed of a mass or body of an elastomeric material, such as medical grade silicone rubber, so that it is substantially rigid. The body of the tip section includes a hollow portion in which various components (to be described later) are located. The inflatable intermediate section 28 is a generally hollow tubular member which is flexible and flaccid in its normal or unactivated state, but is arranged when inflated (pressurized) to become rigid, hard and generally linear. In such a case the three sections making up the cylinder of the prosthesis act like a cantilevered beam, with rear section 26 serving to anchor the intermediate and tip sections of the prosthesis to the body, thereby rendering the penis erect.

As will be fully appreciated from the description to follow the prosthesis 20 of the subject invention is a completely self-contained unit and does not require the use of remotely implanted reservoir/valve/pump arrangements for causing the device to become erect. Thus, each cylinder 22 includes the actuating means for causing the penis to become erect and for allowing the penis to become flaccid when the erection is no longer desired. Moreover, and quite significantly, the subject prosthesis does not require the use of a manually squeezable pump (whether implanted remotely of the cylinder or included within the cylinder itself) to cause the prosthesis to become erect. In this regard the means for effecting the erection of the prosthesis 20 operates in response to the slight displacement (twisting) of a portion of the cylinder to be described later. When that portion of the cylinder is displaced (twisted) back to its original position the prosthesis becomes flaccid. This feature enables the prosthesis 20 to be quite simple in operation, thereby closely simulating the natural erection process.

As shown clearly in FIG. 1 the basic components of the prosthesis 20 are an actuating assembly 30, a fluid reservoir assembly 32, and the heretofore identified inflatable section 28. The actuating assembly will be described in detail later. Suffice for now to state that the actuating assembly is located within the tip section 24 of the cylinder 22 and includes a portion (to be described later) arranged to be twisted (rotated through an acute angle) with respect to the longitudinal axis 152 of the cylinder. This twisting action causes another portion of the actuating means (also to be described later) to move longitudinally down the tip section (i.e., toward the intermediate section) a short distance to cause the displacement of a substantial volume of an operating fluid from the reservoir assembly 32 into the inflatable section 28.

The inflatable section 28 basically comprises a tubular member which is inflatable, but is non-distendable. In a preferred embodiment the tubular chamber is formed of a sleeve 36 of woven Dacron mesh which has been impregnated with an elastomeric material, such as medical grade silicone rubber. As can be seen in FIG. 1 the rear end of the sleeve 36 is closed at 38 while its front end 40 is open to form an open ended chamber. The open front end 40 is in fluid communication with a reservoir chamber (to be described later) of the reservoir assembly 32 and containing the prosthesis' operating liquid 42, e.g., silicone liquid. In the preferred embodiment the chamber 28 is approximately 10 mm in diameter and 7 cm long. Since the material making up the inflatable chamber 28 is flexible but non-distendable, the chamber is flaccid and limp when partially filled with the operating liquid (as is the case prior to activation of the prosthesis as shown in FIGS. 1 and 2). However, when the chamber 28 is fully filled and pressurized by the operating liquid (as is the case after actuation of the prosthesis as shown in FIG. 3) the intermediate section 28 becomes rigid and hard.

As shown clearly in FIGS. 1, 2 and 3 the fluid reservoir assembly 32 basically comprises a tubular body 100 formed of a rigid plastic and having a circular sidewall 102 extending a substantial length of said tip section 24 and located between the actuating assembly 30 and the inflatable chamber 28. The tubular body includes an intermediate wall 104 perpendicularly oriented with respect to the sidewall 102 and having a central opening 106 serving as the entrance to a longitudinally extending tube 108 projecting from the intermediate wall. In a preferred embodiment the central tube 108 is approximately 25 mm long.

The intermediate wall 104 and the circular sidewall 102 collectively define a front chamber 110 and a rear chamber 112, with the latter serving as the operating fluid reservoir of the prosthesis. A moveable piston 114 is located within the front chamber at the front 116 thereof. The piston 114 includes a piston head 118 of generally conical shape and formed of a resilient material, e.g., neoprene rubber. The piston head 118 is fixedly mounted on a linearly displaceable element 120 of the actuating assembly so that it moves longitudinally down the chamber 110, i.e., toward the intermediate section 28, when the element 120 is moved toward the rear of the cylinder 20 and moves up the chamber when the element 120 is returned to its normal forwardly located position.

The front chamber 110 is of a diameter (e.g., 9 mm) which is substantially close to the diameter of the cylinder 22 and is of a relatively short length (e.g., 5 mm) whereupon its volume capacity is 0.39 ml and is filled with a suitable hydraulic fluid, e.g., a silicone liquid, such as type DC 550 sold by Dow Corning.

The fluid reservoir assembly 32 also includes a second moveable piston 122. To that end the second piston 122 includes an elongated piston rod or shaft 124 extending the length of the tube 108 so that its free end 126 is located at the outlet 106 of the hydraulic chamber 110. The piston 122 also includes a piston head 128 which is fixedly mounted at the opposite end of the shaft and within the reservoir 112. The piston head 128 includes a circular sidewall portion 130 extending back over the tube 108 toward the intermediate wall 104 and terminating in a radially extending flanged portion 132 located immediately adjacent the intermediate wall. A ring-like resilient sealing gasket 134 is disposed about the free end of the piston shaft 124 and located within an annular recess 136 therein. The gasket prevents the leakage of hydraulic fluid from the chamber 110 into the interface between the surface of the piston rod 124 and the tube 108.

As can also be seen in the reservoir 112 an annularly shaped hollow member defined between the sidewall 102, the intermediate wall 104 and the tube 108. The rear end of the reservoir 112 is open and connected to and in fluid communication with the open end 40 of the inflatable chamber 28. The chamber 112 is filled with the operating fluid, in this case the same type of silicone liquid as in chamber 110.

The piston head 128 is located within the reservoir 112 and is arranged to be moved down the reservoir in automatic response to the movement of the first piston 114. That action occurs as follows: when the element 120 is moved to the rear, as will be described later, the piston 114 is moved from the position shown in FIGS. 1 and 2 down the short length of the chamber 110 to the position shown in FIG. 3. This action forces approximately 0.39 ml of the hydraulic liquid out of the chamber 110 and against the free end of the piston 122 causing the piston to move. The volumetric capacity of the interior of the tube 108 is slightly less than or equal to the capacity of the hydraulic chamber 110 but its diameter is substantially less, e.g., 3–4 mm, thus the piston 122 moves down tube 108 a much greater distance, e.g., 25 mm, than the distance that piston 114 moves, whereupon a substantially greater volume, e.g., 1.5 ml, of operating fluid located in reservoir 112 is forced into the inflatable chamber 28. In addition a portion of the piston 122 moves into the chamber 28. This action causes that chamber to move from a non-erect, flaccid state like that shown in FIG. 2, to an erect, rigid and linear state like that shown in FIG. 3.

When the element 120 is retracted back toward the tip of the cylinder, an action to be described later, the front end piston 114 is moved toward the tip of the prosthesis again, whereupon hydraulic chamber 110 refills with the hydraulic fluid, so that piston 130 again moves to the front of reservoir 112 and the reservoir again fills with the operating liquid, thus depressurizing the inflatable chamber 28, whereupon the intermediate section 28 of the prosthesis becomes flaccid once again (i.e., assumes the position shown in FIG. 2).

In order to preclude the egress of the operating fluid between the piston head 128 and the circular side wall 102 a second, ring-like resilient sealing gasket 140 is employed. That gasket is mounted on the flanged portion 132 of the piston head.

As can be seen clearly in FIG. 1 the tail section of the prosthesis basically comprises a solid body, also preferably formed of a medical grade silicone rubber, and having a front portion 142 and a tapering rear portion 144. A plurality of longitudinally spaced, annular recesses 146 are provided in the surface of the rear portion 144 of the tail section. These recesses serve as convenient locations for severing a portion of the rear section away from the remainder of the cylinder 22 to configure the prosthesis to the appropriate size for the penis into which it will be implanted.

The details of the actuating assembly 30 will now be described. As can best be seen in FIG. 6 the assembly 30 basically comprises a rotary actuator member 150 and the heretofore identified element 120. The rotary actuator member 150 is a cap-like body which is formed of a rigid material, e.g., plastic end is coupled by cam means to the fixed cylindrical body member 100 in a manner to be described in detail later. The coupling between the two allows the cap member 150 to be rotated or twisted through an acute angle, e.g., approximately 15°, about the longitudinal axis 152 of the cylinder, while holding it at a fixed longitudinal position therealong. In particular, the element 120 is coupled via cam means 154 to the member 150 to enable the element 120 to move down axis 152 (i.e., toward section 28) in response to the rotation or twisting of the cap member 150 in one rotational direction and to move up the axis in response to its rotation or twisting in the opposite rotational direction.

The cap 150 is formed a cylindrical member having a generally domed free end 156 and a cylindrical bore 158 in its opposite end. The shape of the cap-like actuator 150 can be configured as desired to facilitate the securement of it with respect to the penis to minimize relative movement therebetween when the prosthesis is implanted therein. As will be appreciated from the description of the operation of the prosthesis to follow such securement is of considerable importance inasmuch as operation of the prosthesis is based on a slight manual twisting action of the penis being imparted to the actuator cap.

As can be seen in FIG. 6 the member 120 is a cylindrical member whose outside diameter is slightly less than the inside diameter of the bore 158 so that the member 120 can slide freely longitudinally therein along axis 152. The cam means 154 basically comprises a cam track 160 and a cam pin or follower 162. The cam track is an elongated recess in the periphery of the member 120 and extending at an acute angle to the axis 152. The cam pin 162 is fixedly secured to the actuator cap 150 and extends through a hole 164 therein so that its free end is located within the cam track. At each end of the cam track there is a slight recess 164 which serves as locking means for holding the cam pin in place thereat.

In order to secure the cap 150 to the body element 100 to permit twisting motion with respect thereto while precluding longitudinal motion, the body portion 100 includes a pair of slots 168 which are oriented perpendicularly to the axis 152. A pair of mounting pins 170 are fixedly secured in respective holes 172 in the actuator cap 150 at diametrically located positions. The free end of each pin is arranged to be received within an associated slot 168 of the body member 100 so that each pin slides therein when the cap is rotated (twisted).

As will be appreciated by those skilled in the art, the user of the prosthesis merely has to manually grasp or grip the tip of his penis while pulling on it slightly and then rotating or twisting it slightly through a small acute angle, e.g., 15°. This action frees the cam pin from recess 166 and imparts the twist to the actuator cap 150 which causes the cam pin 162 to slide in down cam track 162 from its locked position within recess 166, as shown in FIG. 2, to the opposite end of the cam track, as shown in FIG. 3. The sliding of the cam pin in the track causes the member 120 to move longitudinally down the axis 152, thereby carrying the piston head 118 with it. This later action causes the inflation of the intermediate section 28 as described heretofore. When the actuator cap 150 is rotated to the erect position shown in FIG. 3 the cam pin 162 is received within the locking recess 166 at that end of the cam track. Hence the prosthesis remains in erect condition until it is manually deactivated. Such deactivation occurs by the user merely pulling slightly on the tip of his penis and then twisting it slightly in the opposite direction to cause the pin 162 to move out of its locking recess and then down the track to the opposite end thereof whereupon it becomes locked in place. This reverse twisting action has the effect of pulling the piston head 114 back toward the tip of the prosthesis, whereupon the actuating fluid flows from the intermediate section 28 back into the reservoir 112, whereupon the intermediate section becomes flaccid.

As will be appreciated from the foregoing the device of the instant invention is simple in construction and can be readily and efficiently operated.

Without further elaboration, the foregoing will so fully illustrate my invention that others may, by applying current or future knowledge, readily adopt the same for use under various conditions of service.

I claim:

1. An implantable penile prosthesis comprising an elongated cylinder for disposition within the penis and having a longitudinal axis, said cylinder having a front portion for disposition in the distal portion of the penis, a rear portion for disposition inside the proximal portion of the penis and a hollow inflatable section located therebetween, said cylinder including manually operable actuating means comprising displacement means for moving longitudinally a first predetermined distance toward one end of said cylinder, a hydraulic chamber of a first predetermined volume and having a hydraulic fluid therein, first moveable piston means coupled to said displacement means, fluid reservoir means coupled to said inflatable section, said fluid reservoir means being of a second predetermined volume and having an operating fluid therein, said second volume being substantially greater than said first volume, second piston means coupled to said hydraulic chamber, said first piston means moving in response to the movement of said displacement means for forcing said hydraulic fluid to be expelled from said hydraulic chamber, whereupon said second piston means moves for forcing said operating fluid in said fluid reservoir means into said inflatable section to pressurize said inflatable section, whereupon said section moves from a non-erect, flaccid state to an erect, rigid state.

2. The prosthesis of claim 1 wherein said displacement means comprises rotatable means adapted to be rotated through a predetermined angle about said longitudinal axis from a first rotary position to a second rotary position, whereupon said displacement means moves said first predetermined distance.

3. The prosthesis of claim 2 wherein said rotatable means includes locking means to hold said rotatable means in said second rotary position.

4. The prosthesis of claim 2 wherein said rotatable means is also rotatable about said axis to return it to said first rotary position from said second rotary position, whereupon said displacement means moves said first predetermined distance toward the opposite end of said cylinder.

5. The prosthesis of claim 4 wherein said rotatable means includes locking means to hold said rotatable means in either said first or second rotary positions.

6. The prosthesis of claim 5 wherein said first piston means is arranged to move through a first predetermined length of said hydraulic chamber, and wherein said second piston means is arranged to move a second predetermined length through said fluid reservoir means in response to the movement of said first piston means, said second predetermined length being substantially greater than said first predetermined length.

7. The prosthesis of claim 6 wherein said hydraulic chamber is located adjacent said displacement means and wherein said fluid reservoir means is located between said hydraulic chamber and said inflatable section.

8. The prosthesis of claim 7 wherein said fluid reservoir means comprises an elongated cylindrical chamber extending along the longitudinal axis of said cylinder and including a central passageway extending a substantial distance therethrough, said second piston means comprising an elongated piston shaft and a piston head, said piston shaft extending through said passageway, said hydraulic chamber being in fluid communication with said central passageway, said piston head being located within said cylindrical chamber, whereupon the expulsion of said hydraulic fluid from said hydraulic chamber causes said second piston to move down said cylindrical chamber to force said second fluid into said inflatable section.

9. The prosthesis of claim 8 additionally comprising sealing means for preventing the leakage of said hydraulic fluid and said operating fluid.

10. The prosthesis of claim 9 wherein said hydraulic fluid comprises a silicone liquid.

11. The prosthesis of claim 2 wherein said actuating means is located within said front portion of said cylinder and wherein when said rotary means is rotated from said first rotary position to said second rotary position said displacement means moves said first predetermined distance toward the rear portion of said cylinder.

12. The prosthesis of claim 11 wherein said rotatable means is also rotatable about said axis to return it to said first rotary position from said second rotary position, whereupon said displacement means moves said first predetermined distance toward the front portion of said cylinder.

13. The prosthesis of claim 1 wherein said first piston means is arranged to move through a first predetermined length of said hydraulic chamber, and wherein said second piston means is arranged to move a second predetermined length through said fluid reservoir means in response to the movement of said first piston means, said second predetermined length being substantially greater than said first predetermined length.

14. The prosthesis of claim 13 wherein said hydraulic chamber is located adjacent said displacement means and wherein said fluid reservoir means is located between said hydraulic chamber and said inflatable section.

15. The prosthesis of claim 14 wherein said fluid reservoir means comprises an elongated cylindrical chamber extending along the longitudinal axis of said cylinder and including a central passageway extending a substantial distance therethrough, said second piston means comprising an elongated piston shaft and a piston head, said piston shaft extending through said passageway, said hydraulic chamber being in fluid communication with said central passageway, said piston head being located within said cylindrical chamber, whereupon the expulsion of said hydraulic fluid from said hydraulic chamber causes said second piston to move down said cylindrical chamber to force said second fluid into said inflatable section.

16. The prosthesis of claim 15 additionally comprising sealing means for preventing the leakage of said hydraulic fluid and said operating fluid.

17. The prosthesis of claim 16 wherein said hydraulic fluid comprises a silicone liquid.

18. The prosthesis of claim 1 wherein said inflatable section is flexible but non-distendible.

19. The prosthesis of claim 1 wherein said rear portion is rigid.

20. The prosthesis of claim 19 wherein said rear portion includes means for facilitating the sizing thereof to configure said cylinder to the size of the penis in which it is to be implanted.

21. The prosthesis of claim 1 including sealing means between the hydraulic fluid and the operating fluid for always maintaining said fluids separate from each other.

* * * * *